United States Patent
Barkeley et al.

(10) Patent No.: US 11,178,920 B2
(45) Date of Patent: *Nov. 23, 2021

(54) PATIENT-WARMING GOWN

(71) Applicant: Medline Industries, Inc., Northfield, IL (US)

(72) Inventors: Brian Barkeley, Chicago, IL (US); Stuart Mintz, Glenview, IL (US); Zachary Zott, Chicago, IL (US); Robert Lockwood, Libertyville, IL (US)

(73) Assignee: Medline Industries, LP, Northfield, IL (US)

(*) Notice: Subject to any disclaimer, the term of this patent is extended or adjusted under 35 U.S.C. 154(b) by 114 days.

This patent is subject to a terminal disclaimer.

(21) Appl. No.: 16/552,704

(22) Filed: Aug. 27, 2019

(65) Prior Publication Data
US 2019/0380400 A1    Dec. 19, 2019

Related U.S. Application Data

(63) Continuation of application No. 15/371,377, filed on Dec. 7, 2016, now Pat. No. 10,441,006.

(Continued)

(51) Int. Cl.
*A41D 13/002* (2006.01)
*A41D 13/12* (2006.01)
(Continued)

(52) U.S. Cl.
CPC ..... *A41D 13/0025* (2013.01); *A41D 13/1245* (2013.01); *A41D 13/0051* (2013.01); *A61F 2007/0018* (2013.01)

(58) Field of Classification Search
CPC ........... A41D 13/0025; A41D 13/1245; A41D 13/0051; A61F 2007/0018
(Continued)

(56) References Cited

U.S. PATENT DOCUMENTS 5,735,890 A    4/1998   Kappel
5,792,216 A    8/1998   Kappel
(Continued)

OTHER PUBLICATIONS

3M Infection Prevention Bair Paws Gown; 3M; http://solutions.3m.com/wps/portal/3M/en_EU/Healthcare-Europe/EU-Home/Products/InfectionPrevention/Patient_Warming/Bair_Paws/Bair_Paws_Gown; product presently believed to have been publicly available since at least before Sep. 2, 2015.

(Continued)

*Primary Examiner* — Anne M Kozak
(74) *Attorney, Agent, or Firm* — Fitch, Even, Tabin & Flannery LLP

(57) ABSTRACT

A non-inflating flexible warm air distribution manifold that attaches to the patient side of patient gown. This manifold is configured to receive warmed air the of the warm-air receiving orifice and to distribute the warm air over a wide area of the patient side of the gown. By one approach the manifold comprises a flexible baffle. This baffle can be disposed on the patient side of the gown office proximal (in fact, opposite) the warm-air receiving orifice. The baffle has two or more sides that are secured to the gown and two or more sides that are not secured to the gown. Warm air entering the gown through the warm-air receiving orifice can readily pass through the sides that are not secured to the gown while the warm air entering the gown is largely impeded from passing through the sides that are secured to the gown.

11 Claims, 4 Drawing Sheets

Related U.S. Application Data

(60) Provisional application No. 62/264,053, filed on Dec. 7, 2015.

(51) Int. Cl.
*A41D 13/005* (2006.01)
*A61F 7/00* (2006.01)

(58) Field of Classification Search
USPC .................................................... 2/114
See application file for complete search history.

(56) References Cited

U.S. PATENT DOCUMENTS

| | | | |
|---|---|---|---|
| 5,817,147 A | 10/1998 | Wolf | |
| 5,890,243 A | 4/1999 | Dickerhoff | |
| 5,941,907 A | 8/1999 | Augustine | |
| 6,277,144 B1 | 8/2001 | Tomic-Edgar | |
| 6,994,720 B2 | 2/2006 | Gammons | |
| 7,001,416 B2 | 2/2006 | Augustine | |
| 7,125,417 B2 | 10/2006 | Mizrahi | |
| 7,172,616 B2 * | 2/2007 | Schuessler | A61F 7/0097 607/104 |
| 7,226,454 B2 | 6/2007 | Albrecht | |
| 7,276,076 B2 | 10/2007 | Bieberich | |
| 7,291,163 B2 | 11/2007 | Gammons | |
| 7,364,584 B2 | 4/2008 | Anderson | |
| 7,470,280 B2 | 12/2008 | Bieberich | |
| 7,749,261 B2 | 7/2010 | Hansen | |
| 7,766,950 B2 | 8/2010 | Castellani | |
| 7,819,911 B2 | 10/2010 | Anderson | |
| 7,837,721 B2 | 11/2010 | Augustine | |
| 7,846,192 B2 | 12/2010 | Panser | |
| 7,857,841 B2 | 12/2010 | Anderson | |
| 7,862,599 B2 | 1/2011 | Anderson | |
| 7,871,429 B2 | 1/2011 | Anderson | |
| 7,879,078 B2 | 2/2011 | Vardanega | |
| 7,914,566 B2 | 3/2011 | Anderson | |
| 7,931,682 B2 | 4/2011 | Albrecht | |
| 7,976,572 B2 | 7/2011 | Ziaimehr | |
| 8,025,690 B2 | 9/2011 | Bieberich | |
| 8,043,350 B2 | 10/2011 | Anderson | |
| 8,070,787 B2 | 12/2011 | Panser | |
| 8,097,031 B2 | 1/2012 | Anderson | |
| 8,123,790 B2 | 2/2012 | Bieberich | |
| 8,123,792 B2 | 2/2012 | Bieberich | |
| 8,192,475 B2 | 6/2012 | Anderson | |
| 8,257,415 B2 | 9/2012 | Panser | |
| 8,313,519 B2 | 11/2012 | Anderson | |
| 8,454,672 B2 | 6/2013 | Van Duren | |
| 8,491,645 B2 | 7/2013 | Anderson | |
| 8,597,339 B2 | 12/2013 | Augustine | |
| 8,888,831 B2 | 11/2014 | Van Duren | |
| 9,393,150 B2 | 7/2016 | Pierre | |
| D791,511 S | 7/2017 | Walker | |
| 9,969,127 B2 | 5/2018 | Ellingboe | |
| 2003/0135251 A1 | 7/2003 | Schuessler | |
| 2003/0195596 A1 | 10/2003 | Augustine | |
| 2005/0143796 A1 * | 6/2005 | Augustine | A41D 13/0025 607/104 |
| 2006/0047332 A1 | 3/2006 | Malmberg | |
| 2006/0122672 A1 | 6/2006 | Anderson | |
| 2006/0184217 A1 | 8/2006 | Van Duren | |
| 2006/0259104 A1 | 11/2006 | Panser | |
| 2017/0065005 A1 * | 3/2017 | Nordstrom | A41D 31/145 |
| 2017/0156416 A1 | 6/2017 | Barkeley | |

OTHER PUBLICATIONS

3M Infection Prevention Patient Warming Product Brochure; 3M; http://multimedia.3m.com/mws/media/7667220/patient-warming-product-brochure.pdf; product presently believed to have been publicly available since at least before May 2011; 56 pages.

* cited by examiner

PATIENT-WARMING GOWN

CROSS-REFERENCE TO RELATED APPLICATION

This application is a continuation of U.S. patent application Ser. No. 15/371,377, filed Dec. 7, 2016 which claims benefit of U.S. Provisional Application No. 62/264,053, filed Dec. 7, 2015, which are all hereby incorporated herein by reference in their entirety.

TECHNICAL FIELD

These teachings relate generally to patient gowns and more particularly to patient-warming gowns.

BACKGROUND

Patient gowns are known in the art. Patient gowns are typically worn by patients in a medical-services environment such as an inpatient or outpatient facility. Patient gowns often include sleeves for the patient's arms with the remaining fabric encircling the patient's body. In many cases the gown includes ties, snaps, or the like in order to permit the gown to be at least somewhat closed on the patient's backside.

Generally speaking, patient gowns serve more to preserve a patient's modesty than to warm the patient. In many cases this design preference yields a satisfactory result. In other application settings, however, maintaining the patient's warmth is important and a typical patient gown's insufficiency to much contribute in these regards causes medical service providers to resort to additional warming approaches.

For example, patient-support pads are available that provide supplemental heat to the patient's body when the patient lies atop the pad. As another example, patient gowns are available that include an inflatable bladder. This inflatable bladder has a plurality of small orifices formed therethrough. Upon inflating the inflatable bladder with warm air, the warm air eventually slowly escapes through the small orifices to help heat the patient while they wear the gown.

These prior art approaches to providing supplemental heat are not without issue and concern. Patient gowns that include an inflatable bladder, for instance, tend to be relatively costly. Bladders can also present a wider range of variances with respect to how much air passes through the bladder at any given area. Those variances, in turn, can present challenges with respect to achieving a relatively even heating effect. Also, inflatable bladders present laundering challenges that may conflict with procedures at some facilities.

BRIEF DESCRIPTION OF THE DRAWINGS

The above needs are at least partially met through provision of the patient-warming gown described in the following detailed description, particularly when studied in conjunction with the drawings, wherein.

Figure 1:
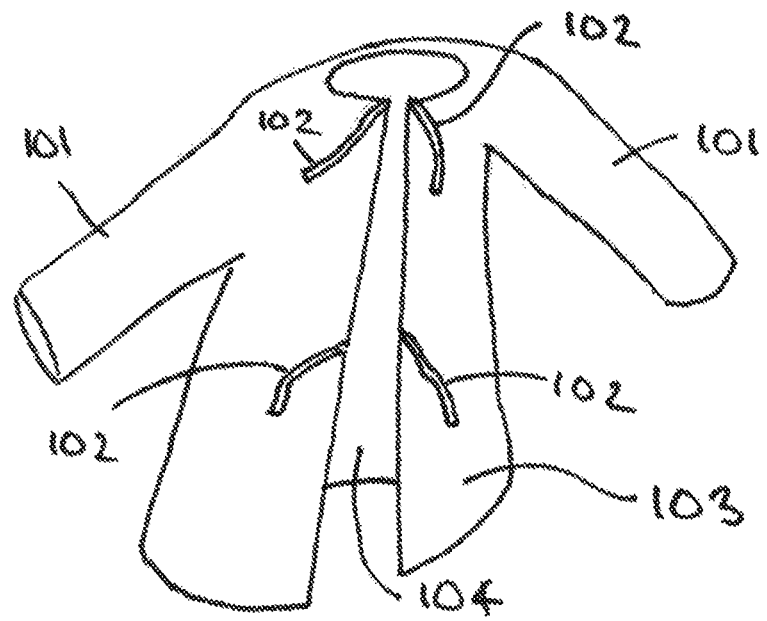
FIG. 1 comprises a backside perspective view as configured in accordance with the prior art.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments are employed with a gown having a patient side and an exterior side and further having a warm-air receiving orifice formed therethrough. The warm-air receiving orifice includes a warm-air tube connector. So configured a flexible conduit can be secured to the warm-air tube connector to thereby permit warm air to be delivered from a warm-air source through the warm-air receiving orifice to the patient side of the gown.

These various embodiments provide a non-inflating flexible warm air distribution manifold that attaches to the patient side of the gown. This manifold is configured to receive warmed air via the warm-air receiving orifice and to distribute the warm air over a wide area of the patient side of the gown.

By one approach the non-inflating flexible warm air distribution manifold comprises a flexible baffle. This flexible baffle can be disposed on the patient side of the gown opposite the warm-air receiving orifice. By one approach the flexible baffle has at least two side edge areas that are at least substantially secured to the gown to thereby form a pneumatic seal. By one approach the flexible baffle also has at least two side edges that are not at least substantially secured to the gown and which hence form a pneumatic pathway such that warm air entering the gown through the warm-air receiving orifice can readily pass through the sides that are not secured to the gown (while the warm air entering the gown is largely impeded from passing through the sides that are secured to the gown).

By one approach the flexible baffle is comprised of fabric. This can be a fabric that is identical to the fabric that comprises the gown or not as desired.

By one approach the two sides of the flexible baffle that are at least substantially secured to the gown comprise two opposing sides of the flexible baffle. For example, the top and bottom edges of the flexible baffle can comprise the sides that are secured to the gown.

By one approach the flexible baffle further includes one or more slits formed therethrough. By one approach these splits extend between the two sides of the flexible baffle that are secured to the gown and may be, for example, disposed at least substantially parallel to one another. So configured, warmed air entering the gown through the warm-air receiving orifice can also pass through the flexible baffle via such slits.

If desired, these teachings will also accommodate forming a plurality of small perforations through the flexible baffle. So configured, warmed air entering the gown through the warm-air receiving orifice can also pass through these perforations.

So configured, a patient gown can serve as a ready mechanism to conveniently and inexpensively help to distribute warmed air over and around the patient's body to thereby help maintain an appropriate temperature for the patient. The aforementioned flexible baffle can be permanently secured to the gown or only temporarily secured as desired. In either case the gown and the flexible baffle do not require any particular special handling including during laundering.

Figure 2:
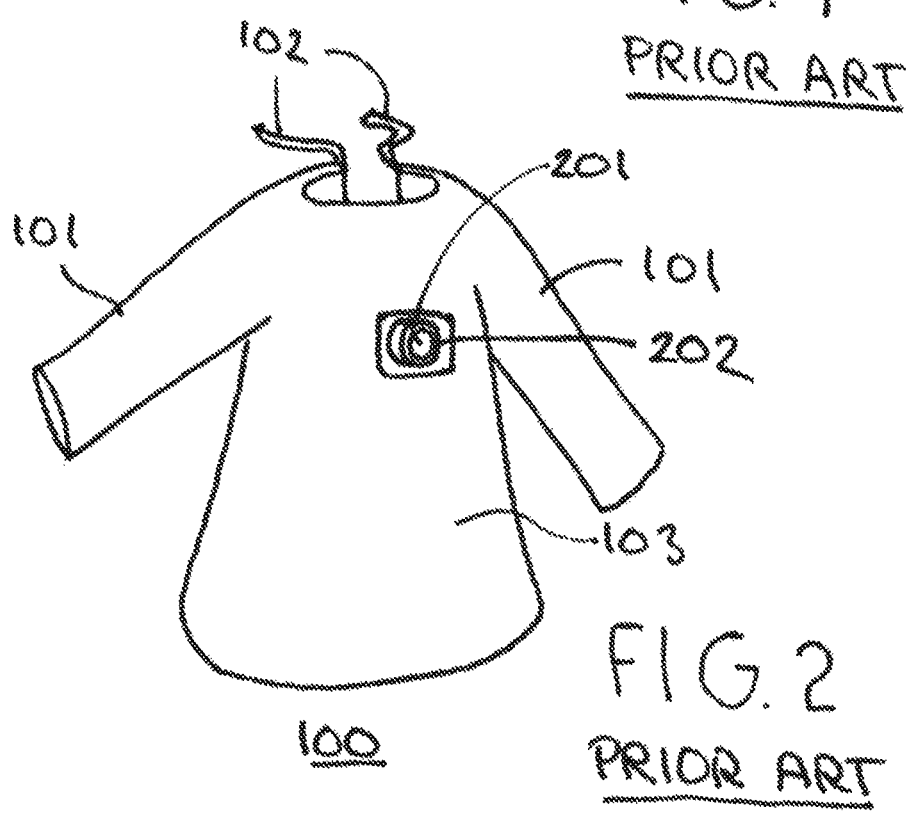
FIG. 2 comprises a front side perspective view as configured in accordance with the prior art.

These and other benefits may become clearer upon making a thorough review and study of the following detailed description. Referring now to the drawings, it may be helpful to first briefly describe and characterize a prior art patient gown 100 that can serve in the present regards. FIGS. 1 and 2 present a patient-warming gown 100 that comprises an open-back gown. This patient-warming gown 100 is formed using a cloth (or other material) fabric of choice and includes sleeves 101 of a desired length for receiving the patient's arms. Strings 102 or the like are provided to tie one or more knots to secure the patient-warming gown 100 in place.

The patient-warming gown 100 includes an exterior side 103 and a patient side 104. In addition, and referring in particular to FIG. 2, the patient-warming gown 100 includes, on the front side thereof, a warm-air receiving orifice 201 formed therethrough, the warm-air receiving orifice 201 having (and indeed, being formed by, in part) a warm-air tube connector 202. So configured, a flexible pneumatic tube (not shown) can be secured to the warm-air tube connector 202 (for example, using a friction fit). When the opposing end of the flexible pneumatic tube connects to an output port of a forced warm air device, warm air can be pushed from the exterior side 103 of the patient-warming gown 100 to the patient side 104 of the patient-warming gown 100.

Choices of materials and design in all the foregoing regards are well understood in the art. Accordingly, for the sake of brevity and as the present teachings are not overly sensitive to any particular selections in the foregoing regards, further elaboration will not be provided here with respect to the gown itself.

Figure 3:
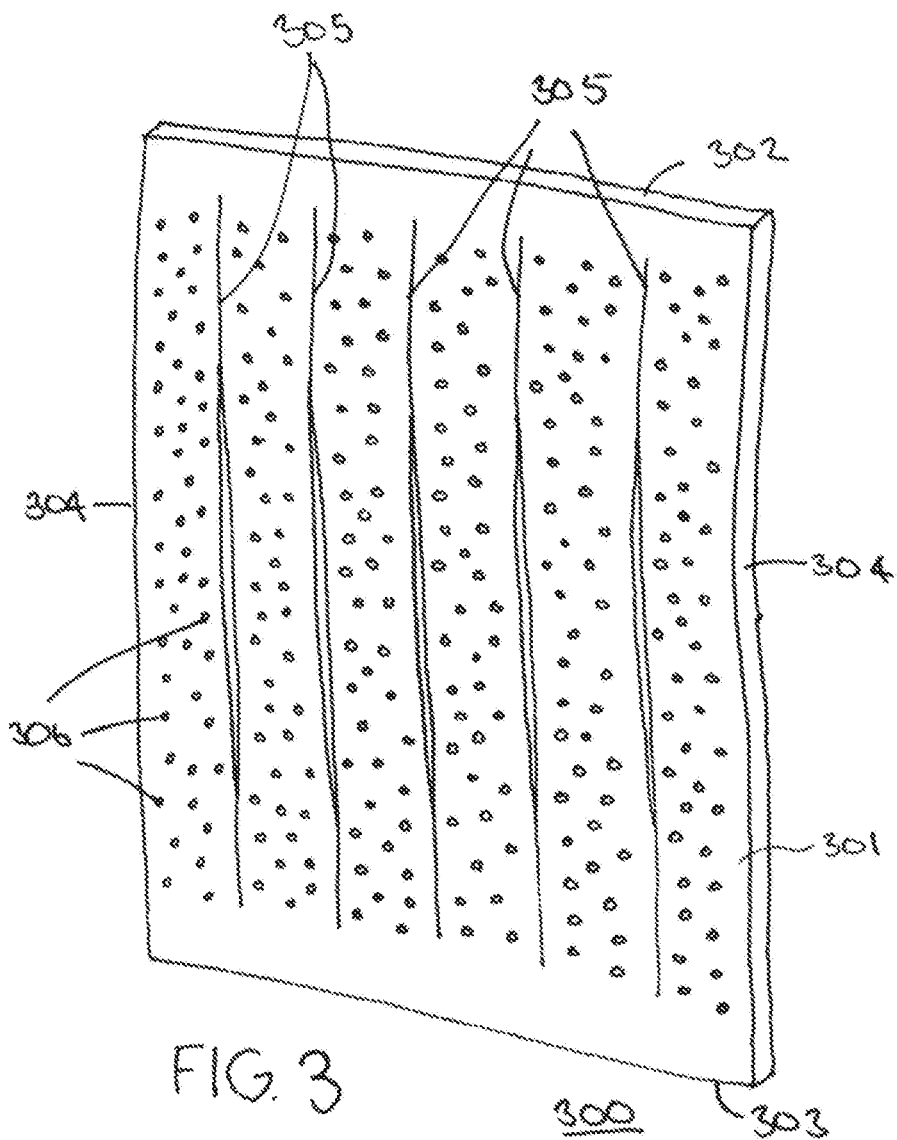
FIG. 3 comprises a perspective view as configured in accordance with various embodiments of these teachings.

Referring now to FIG. 3, these teachings provide for attaching at least one non-inflating flexible warm air distribution manifold to the patient side 104 of the patient-warming gown 100. Generally speaking, this non-inflating flexible warm air distribution manifold is configured to receive warmed air via the aforementioned warm-air receiving orifice 201 and to distribute the warm air over a wide area of the patient side 104 of the patient-warming gown 100. (As used herein, this reference to being "non-inflating" is intended to differentiate this manifold from bladder-based air-distribution approaches. Accordingly, "non-inflating" does not mean that the receipt of air does not result in displacement of material (including material comprising the manifold itself). That said, any such displacement will quickly recede (for example, within 1 to 5 seconds) upon cessation of the receipt of the air as compared to an inflation-based approach where deflation of the inflated component (such as a bladder) requires considerably more than five seconds.)

In this particular illustrative example the non-inflating flexible warm air distribution manifold 300 comprises a flexible baffle 301. This flexible baffle 301 can be comprised of one or more fabric and/or plastic layers as desired. Generally speaking the flexible baffle 301 is substantially resistant to the passage of air therethrough (by blocking, for example, 95% or more of air being presented via a typical prior art warm air source).

In this example the flexible baffle 301 has a rectangular form factor. So configured, the flexible baffle 301 has a top edge 302 and opposing bottom edge 303. Accordingly, the flexible baffle 301 also has opposing side edges 304. The size of the flexible baffle 301 can vary with the particular needs and/or opportunities that characterize a given application setting. The width of the flexible baffle 301 can vary, for example, from about 6 inches to about 18 inches while the length/height of the flexible baffle 301 can vary, for example, from about 12 inches to about 24 inches.

In this illustrative example the flexible baffle 301 further includes at least one (and in this example, five) slits 305 formed therethrough. In this example the slits are disposed at least substantially parallel to one another (i.e., within at least 5° of being parallel one to the other) and extend between the top and bottom edges 302 and 303 of the flexible baffle 301. Also in this example the slits 305 are disposed orthogonally to the top and bottom edges 302 and 303 of the flexible baffle 301 and are disposed equidistant from one another.

By one approach these slits 305 simply comprise a cut through the material comprising the flexible baffle 301. By another approach, these slits 305 are formed at least in part by removing material to thereby form, at least in part, a lateral gap in the material.

If desired, and as illustrated in FIG. 3, the flexible baffle 301 can further include a plurality of small perforations (a few of which are denoted by reference numeral 306) formed therethrough. In a typical application setting there will be considerably more perforations 306 than slits 305. Accordingly, there will typically be a large plurality of these perforations 306 between each adjacent pair of the slits 305.

The perforations 306 can comprise small holes having a diameter or other relevant cross-section no greater than ⅛ of an inch. By one approach the perforations 306 can all have an identical shape and size. By another approach at least some of the perforations 306 can have a different shape and/or a different size to best suit, for example, the needs of a particular application setting.

Figure 4:
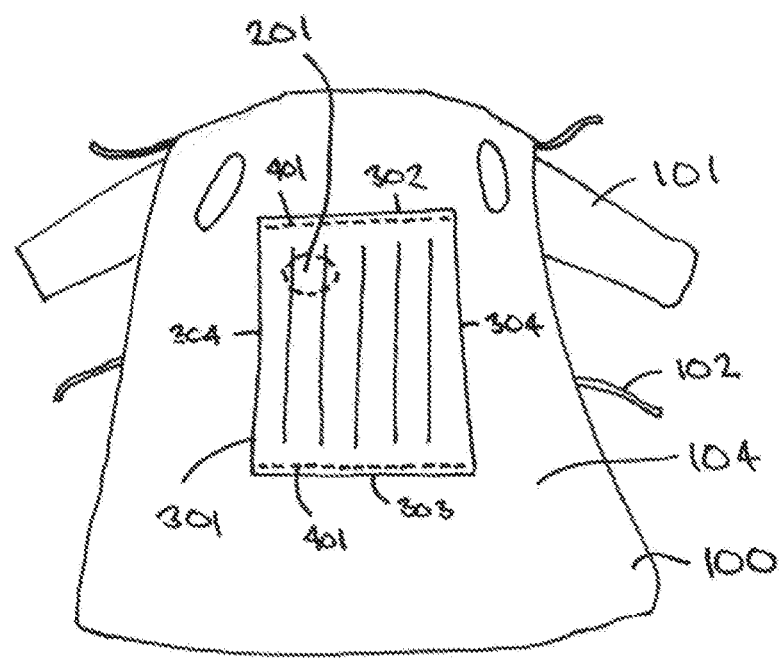
FIG. 4 comprises a backside elevational view as configured in accordance with various embodiments of these teachings.

Referring now to FIG. 4, the flexible baffle 301 is disposed on the patient side 104 of the patient-warming gown 100 opposite the warm-air receiving orifice 201. Being "opposite" does not require that the flexible baffle 301 be centered with respect to the warm-air receiving orifice 201. Instead, if desired and as illustrated, the flexible baffle 301 can be disposed opposite the warm-air receiving orifice 201 in an off-center manner as shown.

More particularly, the flexible baffle 301 is attached to the patient side 104 of the patient-warming gown 100. More specifically, in this example the flexible baffle 301 is at least substantially secured to the patient-warming gown 100 at the top and bottom sides of the flexible baffle 301. In this example the flexible baffle 301 is attached to the patient-warming gown 100 via stitching 401. These teachings will accommodate other permanent and temporary forms of attachment including adhesives, staples, hooks-and-loops (such as Velcro fasteners), and so forth.

In addition, the flexible baffle 301 is specifically not attached to the patient-warming gown 100 on or near the remaining two sides 304. (If desired, small portions (for example, up to 10 or 15%) of these two sides 304 can be attached to the patient-warming gown 100 if desired, but generally speaking the bulk of these two sides 304 remain unattached.) So configured, the secured sides form a pneumatic seal that will resist the passage of air therethrough while the unattached sides form a pneumatic pathway such that warm air entering the patient-warming gown 100 through the warm-air receiving orifice 201 can readily pass through the unattached sides. (As used herein it will be understood that these references to a "pneumatic seal" do not require a complete seal but will instead accommodate a range of sealing from complete to about 75 percent complete.)

Figure 5:
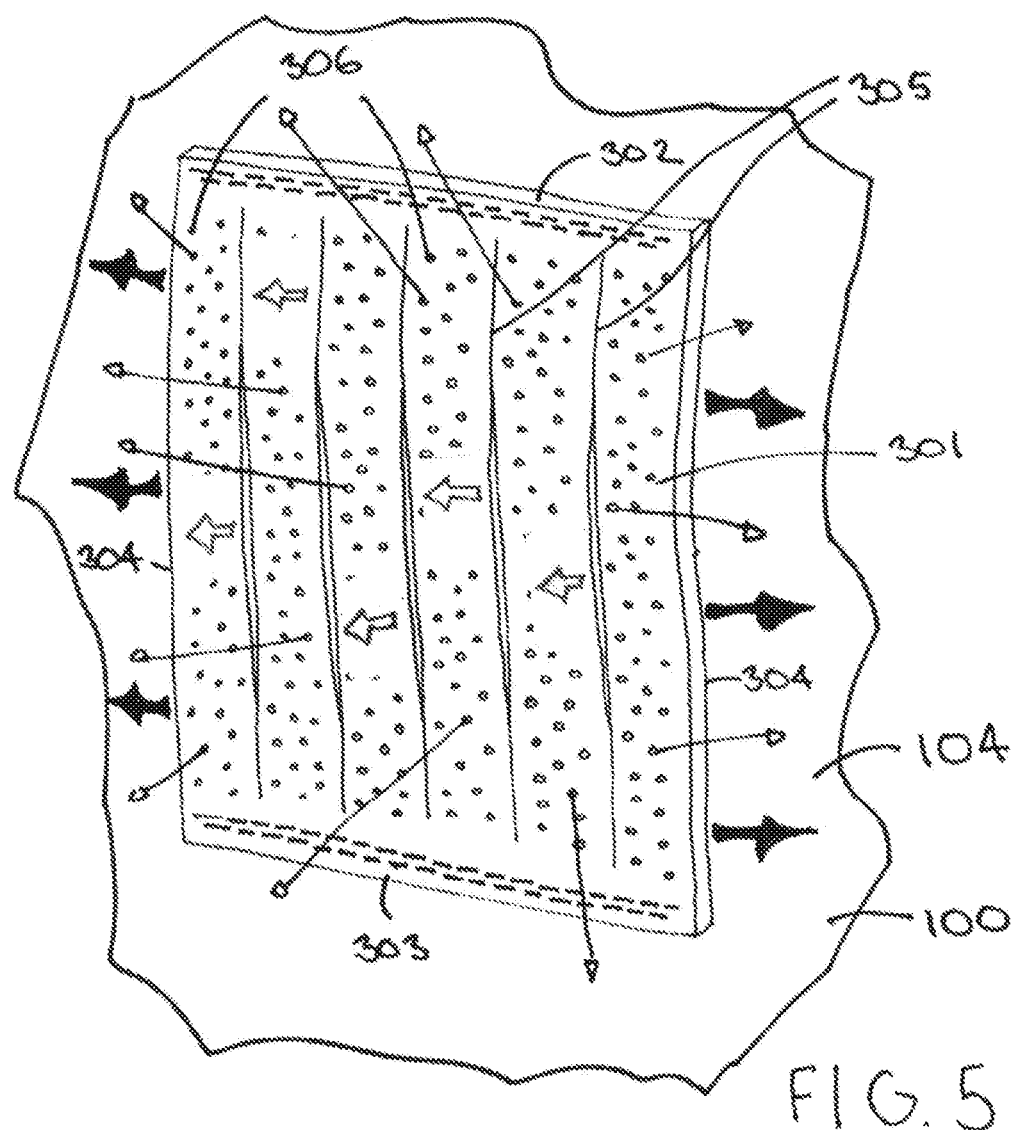
FIG. 5 comprises a perspective view as configured in accordance with various embodiments of these teachings.

FIG. 5 provides a more detailed view in these regards. In this example warmed air enters on the patient side 104 of the patient-warming gown 100 through the aforementioned warm-air receiving orifice 201 and encounters the flexible baffle 301. Some of the warmed air will pass around the flexible baffle 301 via the unattached sides as indicated by the solid-black block arrowheads. Some of the warmed air will pass through the flexible baffle 301 via the aforementioned slits 305 as indicated by the non-solid-black block arrowheads. And some of the warmed air will pass through the flexible baffle 301 via the aforementioned perforations 306 as indicated by the small, narrow arrowheads. In combination the warmed air entering the patient-warming gown 100 is distributed over a wide area of the patient side 104 of the patient-warming gown 100. (As used herein, this reference to a "wide area" will be understood to refer to a range of coverage from about 15 percent to about 100 percent coverage.)

Figures 6, 7, 8:
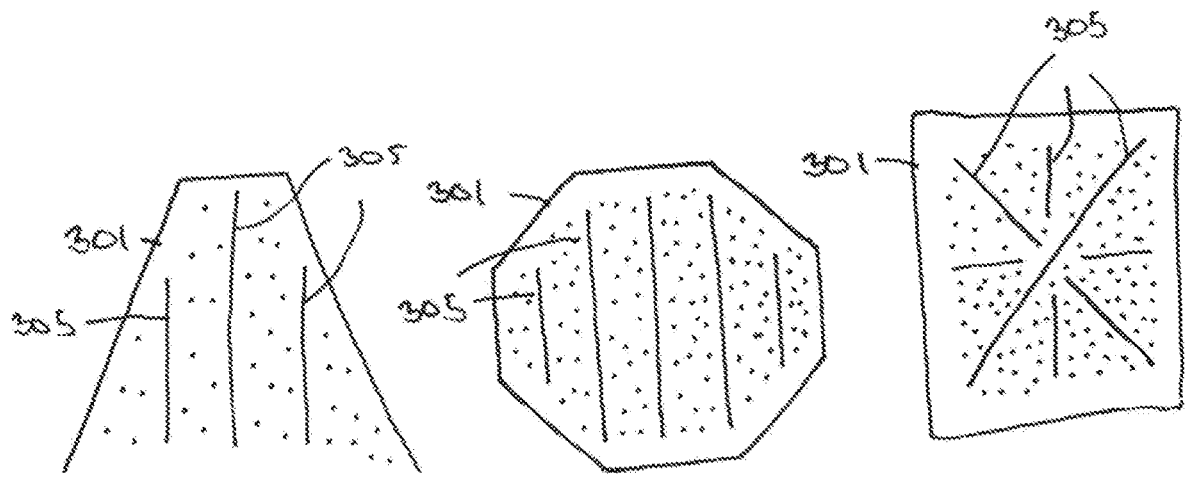
FIG. 6 comprises a front elevational view as configured in accordance with various embodiments of these teachings.
FIG. 7 comprises a front elevational view as configured in accordance with various embodiments of the invention.
FIG. 8 comprises a front elevational view as configured in accordance with various embodiments of these teachings.

These teachings are highly flexible in practice and will accommodate a wide variety of modifications to suit the needs of a particular application setting. FIGS. 6, 7, and 8 illustrate, for example, that the flexible baffle 301 can have any of a variety of form factors, and that the slits 305 need not all have a same length, be parallel to one another, or be orthogonal to the attached sides of the flexible baffle 301.

So configured, the non-inflating flexible warm air distribution manifold can be inexpensively yet reliably and effectively provided using only inexpensive materials and simple manufacturing techniques. Notwithstanding this relatively inexpensive approach, the resultant manifold can be highly effective at appropriately distributing warmed air as desired. Also, the resultant components are readily and easily laundered without any particular special care being required regardless of whether the manifold is permanently or temporarily attached to the patient-warming gown.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A patient-warming gown, comprising: a gown comprised of a first fabric and having an inner side configured to be worn next to a patient and an exterior side, the gown having a warm-air receiving orifice formed therethrough, the warm-air receiving orifice having a warm-air tube connector; a flexible baffle comprised of a second fabric and disposed on the inner side of the gown opposite the warm-aft receiving orifice, the flexible baffle having at least two secured sides that are secured to the gown and at least two non-inflatable unsecured sides that are not secured to the gown to thereby form pneumatic pathways via the unsecured sides such that some warm air entering the gown through the warm-air receiving orifice can readily pass through the unsecured sides while the secured sides present a pneumatic seal that resists a flow of aft, wherein the flexible baffle further includes a plurality of slits formed therethrough, wherein the plurality of slits do not all have a same length.

2. The patient-warming gown of claim 1 wherein the first fabric is the same as the second fabric.

3. The patient-warming gown of claim 1 wherein the first fabric is different from the second fabric.

4. The patient-warming gown of claim 1 wherein the flexible baffle is shaped as a triangle having at least one truncated corner.

5. The patient-warming gown of claim 1 wherein the flexible baffle is shaped as an octagon.

6. The patient-warming gown of claim 1 wherein at least one of the plurality of slits is disposed at a 45 degree angle to at least another one of the plurality of slits.

7. The patient-warming gown of claim 1 wherein at least some of the slits comprising the plurality of slits are disposed at least substantially parallel to one another.

8. The patient-warming gown of claim 7 wherein all of the slits comprising the plurality of slits are disposed at least substantially parallel to one another.

9. The patient-warming gown of claim 1 wherein the flexible baffle further includes a plurality of holes formed therethrough.

10. The patient-warming gown of claim 9 wherein the holes comprising the plurality of holes each have a cross-section that does not exceed ⅛th of an inch.

11. The patient-warming gown of claim 10 wherein the cross-section comprises a diameter of each hole.

* * * * *

UNITED STATES PATENT AND TRADEMARK OFFICE
CERTIFICATE OF CORRECTION

PATENT NO. : 11,178,920 B2
APPLICATION NO. : 16/552704
DATED : November 23, 2021
INVENTOR(S) : Brian Barkeley et al.

It is certified that error appears in the above-identified patent and that said Letters Patent is hereby corrected as shown below:

On the Title Page
(71) Applicant: delete "Inc." and insert --LP--.

In the Claims
Claim 1, Column 6, Line 17, delete "warm-aft" and insert --warm-air--.
Claim 1, Column 6, Line 25, after "of", delete "aft," and insert --air,--.

Signed and Sealed this
Ninth Day of August, 2022

Katherine Kelly Vidal
*Director of the United States Patent and Trademark Office*